(12) United States Patent
Kepler et al.

(10) Patent No.: US 8,397,719 B2
(45) Date of Patent: Mar. 19, 2013

(54) PRESSURE SUPPORT SYSTEM WITH UPSTREAM HUMIDIFIER

(75) Inventors: Jeffrey Kepler, Export, PA (US); Chad Kolas, Murrysville, PA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 219 days.

(21) Appl. No.: 12/867,624

(22) PCT Filed: Feb. 25, 2009

(86) PCT No.: PCT/IB2009/050753
§ 371 (c)(1),
(2), (4) Date: Aug. 13, 2010

(87) PCT Pub. No.: WO2009/107070
PCT Pub. Date: Sep. 3, 2009

(65) Prior Publication Data
US 2010/0307495 A1 Dec. 9, 2010

Related U.S. Application Data

(60) Provisional application No. 61/031,519, filed on Feb. 26, 2008.

(51) Int. Cl.
*A61M 16/16* (2006.01)

(52) U.S. Cl. ......... 128/203.27; 128/200.24; 128/203.12; 128/203.15; 128/203.16; 128/203.17; 128/203.26; 128/204.17; 128/204.18; 128/204.21

(58) Field of Classification Search ............. 128/200.24, 128/203.12, 203.15, 203.16, 203.17, 203.26, 128/203.27, 204.17, 204.18, 204.21
See application file for complete search history.

(56) References Cited

U.S. PATENT DOCUMENTS

| | | | | |
|---|---|---|---|---|
| 3,954,920 A | * | 5/1976 | Heath | 261/104 |
| 4,121,583 A | * | 10/1978 | Chen | 128/203.27 |
| 6,349,722 B1 | * | 2/2002 | Gradon et al. | 128/203.17 |
| 6,435,180 B1 | * | 8/2002 | Hewson et al. | 128/204.18 |
| 2004/0221844 A1 | | 11/2004 | Hunt | |

FOREIGN PATENT DOCUMENTS

| | | |
|---|---|---|
| EP | 1655052 A2 | 5/2006 |
| WO | WO02066106 A1 | 8/2002 |
| WO | WO2007038152 A2 | 4/2007 |
| WO | WO2007038690 A2 | 4/2007 |

* cited by examiner

*Primary Examiner* — Melanie Hand
*Assistant Examiner* — Andrew S Lo
(74) *Attorney, Agent, or Firm* — Michael W. Haas (57) ABSTRACT

A pressure support system (10) comprises a humidifier (20) adapted to increase the amount of water vapor entrained in a supply of breathing gas, and a positive air pressure device (30) fluidly coupled downstream of the humidifier. The positive air pressure device is structured to generate a positive pressure flow of breathing gas from the supply of breathing gas received from the outlet of the humidifier.

7 Claims, 5 Drawing Sheets

PRESSURE SUPPORT SYSTEM WITH UPSTREAM HUMIDIFIER

CROSS REFERENCE TO RELATED CASES

This application claims the benefit of International Application Number PCT/IB2009/050753, filed Feb. 25, 2009, and U.S. Provisional Application Ser. No. 61/031,519, filed Feb. 26, 2008.

The present invention generally pertains to a pressure support system, and in particular, to a pressure support system having a humidifier connected upstream of a pressure generating device. The present invention also pertains to a method of providing a regimen of respiratory therapy to a patient using a pressure support system with a humidifier connected upstream of a pressure generating device.

There are many instances were it is desirable to deliver, either invasively or non-invasively, a flow of breathing gas to the airway of a patient. For example, many individuals suffer from sleep apnea and other related diseases which result in episodic upper airway obstruction during sleep. As a consequence, the patient experiences repeated sleep interruptions. Pressure support systems, such as positive airway pressure (PAP) devices, have been developed to treat sleep apnea and other related diseases.

A typical PAP device includes a flow generator that generates a positive pressure flow of breathing gas. The positive pressure flow of breathing gas is delivered to the airway of a patient via a patient circuit, which typically includes a delivery conduit and a patient interface device. It is known to deliver the positive pressure flow of breathing gas at a continuous positive airway pressure (CPAP), at a variable airway pressure (such as a bi-level pressure) that changes with the patient's respiratory cycle, or at an auto-titrating pressure that varies with the monitored condition of the patient. Pressure support therapies are also provided to treat other medical and respiratory disorders, such as Cheynes-Stokes respiration, congestive heart failure, and stroke.

Figure 7:
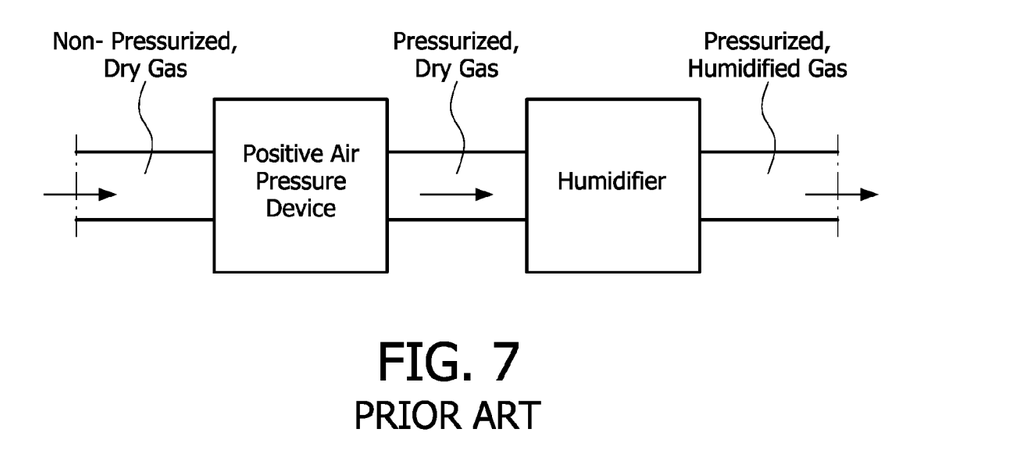
FIG. 7 is a simplified schematic diagram of a known pressure support system.

Providing positive airway pressure to such patients is well known in the art. However, it has been found that breathing dry pressurized air is uncomfortable to the patient. Over time, the positive pressure flow of breathing gas dries out the patient's throat, nasal passages, and mucus membranes resulting in discomfort and pain. To overcome this problem, many prior art pressure support systems include a humidifier adapted to add water vapor to the positive pressure flow of breathing gas. A simplified schematic diagram which illustrates such a prior art pressure support system is found at FIG. 7. As seen in FIG. 7, a PAP device pressurizes a supply of dry breathing gas. This pressurized, dry breathing gas is communicated to a humidifier wherein water vapor is entrained within the pressurized breathing gas (i.e., the breathing gas is humidified). The pressurized, humidified breathing gas can then be delivered to a user. As seen in FIG. 7, the humidifier is located downstream of the PAP device.

One such device exemplary of the art is disclosed in U.S. Pat. No. 5,673,687 to Dobson et al. ("the '687 patent"). The device disclosed in the '687 patent includes a PAP device, a passive humidifier, and a patient circuit. The passive humidifier has a reservoir and a corresponding lid. The reservoir is adapted to be filled with water. The humidifier is connected downstream of the PAP device, between the outlet of the PAP device and the patient circuit. As the patient breaths, the positive pressure flow of breathing gas exits the PAP device and enters the humidifier wherein it passes over the water contained in the reservoir. Water vapor within the reservoir, which is present due to the natural evaporation of the water within the reservoir, is passively entrained within the dry flow of pressurized breathing gas. A humidified flow of breathing gas then exits the humidifier and is delivered to a patient via the patient circuit.

Another such device exemplary of the art is disclosed in U.S. Pat. No. 6,349,722 to Gradon et al ("the '722 patent"). Unlike the passive humidifier employed by the device in the '687 patent, the device described in the '722 patent employs an active humidifier designed to increase the amount of water vapor entrained within the positive pressure flow of breathing gas. The humidifier disclosed in the '722 patent has a water chamber with a plastic top and a metal bottom. The metal bottom is typically formed by stamping a sheet of metal, such as aluminum, which exhibits high thermal conductivity. The bottom of the water chamber is placed on top of a heater plate. Active humidification occurs as the temperature of the heater plate increases above ambient temperature. The heat generated by the heater plate raises the temperature of the water contained within the chamber thereby accelerating the rate of evaporation of the water. As the dry flow of pressurized breathing gas passes over the water contained in the reservoir, water vapor is entrained therein. The humidified flow of breathing gas is then delivered to the patient's airway via the patient circuit.

Generally, as the temperature of a gas increases, so too does the amount of water vapor that can be entrained therein. Conversely, as the temperature of a gas decreases, the amount of water vapor that can be entrained therein also decreases. Both the passive and active humidifiers described above are designed to increase the amount of water vapor entrained within the breathing gas, after the breathing gas is pressurized but before the breathing gas enters a patient circuit. As will be discussed more fully below in conjunction with Table 1, this arrangement increases the risk of rainout (i.e., condensation) within the patient circuit because the water vapor is added to the flow of breathing gas after pressurization. Rainout occurring in the patient circuit is undesirable; rainout occurring within the PAP device is even more undesirable. For example, the air flow path within the PAP device is difficult to access and clean. As a result, rainout occurring within the PAP device is likely to cause the growth of bacteria inside the PAP device. Additionally, the flow path within the PAP device is generally not constructed to be watertight. As a result, rainout occurring within the PAP device is likely to cause water to leak onto and damage the circuitry of the PAP device, and/or likely to cause the flow generator to malfunction, among others. To avoid rainout from occurring within the PAP device, prior art systems locate the humidifier downstream of the PAP device; between the PAP device and the patient circuit. Placement of the humidifier downstream of the flow generator, however, also presents several drawbacks. For example with this arrangement, the humidification chamber is pressurized by the positive pressure flow of breathing gas. As a result, adequate seals must be maintained to prevent air and/or water leakage from the humidifier. Additionally, a large pressure drop exists across the humidifier. This pressure drop must be accounted for to insure that the flow of breathing gas is delivered to the patient at the desired therapeutic pressure.

As mentioned above, placing the humidifier downstream of the flow generator also increases the potential for rainout to occur inside the patient circuit. Referring now to Table 1 below, the PAP device receives a flow of breathing gas at an ambient temperature of 25° C. (77° F.). Due to the work of compression by the PAP device pressure generator, the temperature of the flow of breathing gas increases to 32° C. (89.6° F.). The humidifier, which is placed downstream of the PAP device, receives the positive pressure flow of breathing gas from the gas discharge of the PAP device. Here the positive pressure flow of breathing gas has been heated approximately 7° C. (approximately 12.6° F.) over ambient prior to entering the humidifier. Because of this temperature increase, the flow of breathing gas is capable of entraining more water vapor therein. This is reflected in Table 1 by drop in the relative humidity of the flow of breathing gas from 50% (at ambient) to 34% (at the gas discharge of the PAP).

TABLE 1

Humidifier Downstream of the Positive Air Pressure Device

| | Water/Air Concentration (mg/L) | Temp. (Deg C.) | Sat. Vapor Pressure (Pa) | Vapor Pressure (Pa) | Humidity (RH %) |
|---|---|---|---|---|---|
| Ambient Air | 11.4 | 25.0 | 3148 | 1569 | 50 |
| Gas Intake (PAP) | 11.4 | 26.0 | 3340 | 1575 | 47 |
| Pressure Generator | 11.4 | 26.0 | 3340 | 1575 | 47 |
| Gas Discharge (PAP) | 11.4 | 32.0 | 4718 | 1606 | 34 |
| Gas Outlet (Humidifier) | 26 | 32.0 | 4718 | 3663 | 78 |
| Wall of Patient Conduit at Patient End | 26 | 26.0 | 3340 | 3591 | 108 |

Because the relative humidity of the flow of breathing gas has been lowered, the humidifier is able to operate more efficiently. As seen in Table 1, the humidifier increases the absolute humidity of the flow of breathing gas from 11.4 mg/L to 26 mg/L (the relative humidity increases from 34% to 78%). Some of this humidification, however, is wasted because the flow of breathing gas cools as it travels through the patient conduit. This cooling allows the water vapor in the flow of breathing gas to reach the dew point and rainout. Here, the temperature of the flow of breathing gas along the wall of the patient conduit cools from 32° C. (89.6° F.) to 26° C. (78.8° F.) causing the relative humidity of the positive pressure flow of breathing gas to exceed 100% (i.e., which means rainout will occur). To prevent the water vapor within the flow of breathing gas from reaching the dew point while within the patient conduit, additional measures such as heating the patient conduit and/or patient interface must be implemented.

Accordingly, a need exists for an apparatus and method for adding water vapor to a flow of breathing gas which prevents rainout within the PAP device and/or patient circuit, and which overcomes these and other problems associated with known systems.

In accordance with an aspect of the present invention, a humidifier is adapted for use with a positive air pressure device structured to generate a positive pressure flow of breathing gas. The humidifier comprises a chamber, a gas inlet, and a gas outlet. The chamber is structured to hold a supply of water having a free water surface. The gas inlet is structured to supply a flow of breathing gas to the chamber. The gas outlet is structured to discharge a humidified flow of breathing gas from the chamber and is adapted to fluidly couple with a gas intake of such a positive air pressure device.

According to another aspect of the present invention, a positive air pressure device comprises a humidifier adapted to produce a humidified flow of breathing gas and a flow generator structured to produce a positive pressure flow of breathing gas, wherein the humidifier is in fluid communication with and disposed upstream of the flow generator.

According to another aspect of the present invention, a pressure support system comprises a humidifier adapted to increase the amount of water vapor entrained in a supply of breathing gas, and a positive air pressure device fluidly coupled downstream of the humidifier, wherein the positive air pressure device is structured to generate a positive pressure flow of breathing gas from the supply of breathing gas.

According to another aspect of the present invention, a method for providing a regimen of respiratory therapy to a user comprises receiving a humidified flow of breathing gas at a gas intake of a positive air pressure device, generating with the positive air pressure device a positive pressure flow of breathing gas in response to receiving the humidified flow of breathing gas, discharging the positive pressure flow of breathing gas from a gas discharge of the positive air pressure device, and delivering the positive pressure flow of breathing gas to such a user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of "a", "an", and "the" include plural referents unless the context clearly indicates otherwise.

As employed herein, the statement that two or more parts are "connected", "coupled", or "attached" shall mean that the parts are joined or operated together either directly or through one or more intermediate parts or components.

As employed herein, the term "absolute humidity" refers to the quantity of water vapor in a particular volume of gas and is generally expressed in units of milligrams per liter (mg/L) throughout.

As employed herein, the term "relative humidity" refers to the amount of water vapor that a gas, at a particular temperature, is holding compared to the amount of water vapor that the gas is capable of holding at that particular temperature. Relative Humidity is generally expressed as a percentage (%) throughout.

As employed herein, the term "rainout" refers to the condensation of water vapor, entrained in a gas, into liquid or solid. Rainout typically occurs when the relative humidity of a gas reaches approximately 100%.

Figure 1:
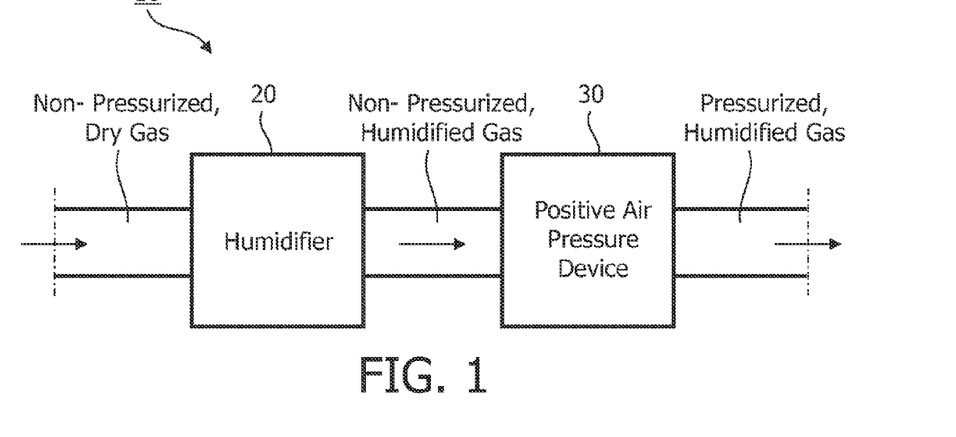
FIG. 1 is a simplified schematic view of a pressure support system according to the principles of the present invention.

FIG. 1 is a simplified schematic diagram of a pressure support system 10 according to the principles of the present invention. Unlike known systems (such as that shown in FIG. 7), pressure support system 10 is arranged such that a humidifier 20 is located upstream of a positive air pressure device 30. As such, humidifier 20 receives a non-pressurized, dry flow of breathing gas and produces a non-pressurized, humidified flow of breathing gas therefrom. Positive air pressure device 30 receives this non-pressurized, humidified flow of breathing gas from humidifier 20 and produces a pressurized, humidified flow of breathing gas therefrom.

Figure 2:
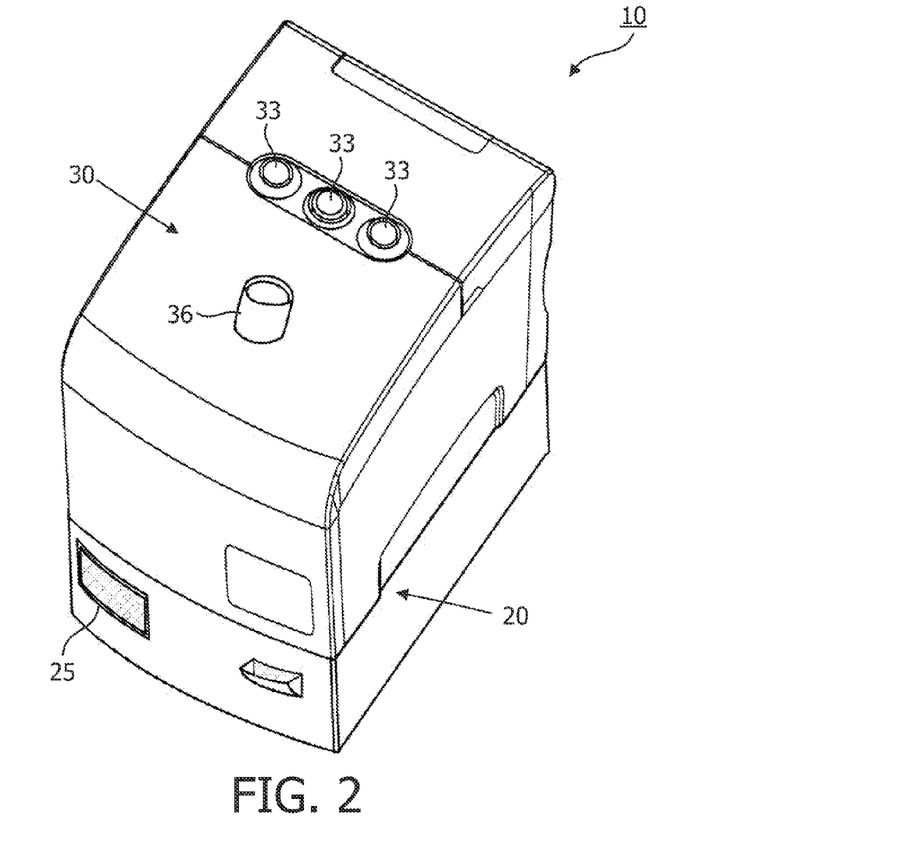
FIG. 2 is a perspective view of a pressure support system adapted to provide a regimen of respiratory therapy to a patient according to one embodiment.
Figure 3:
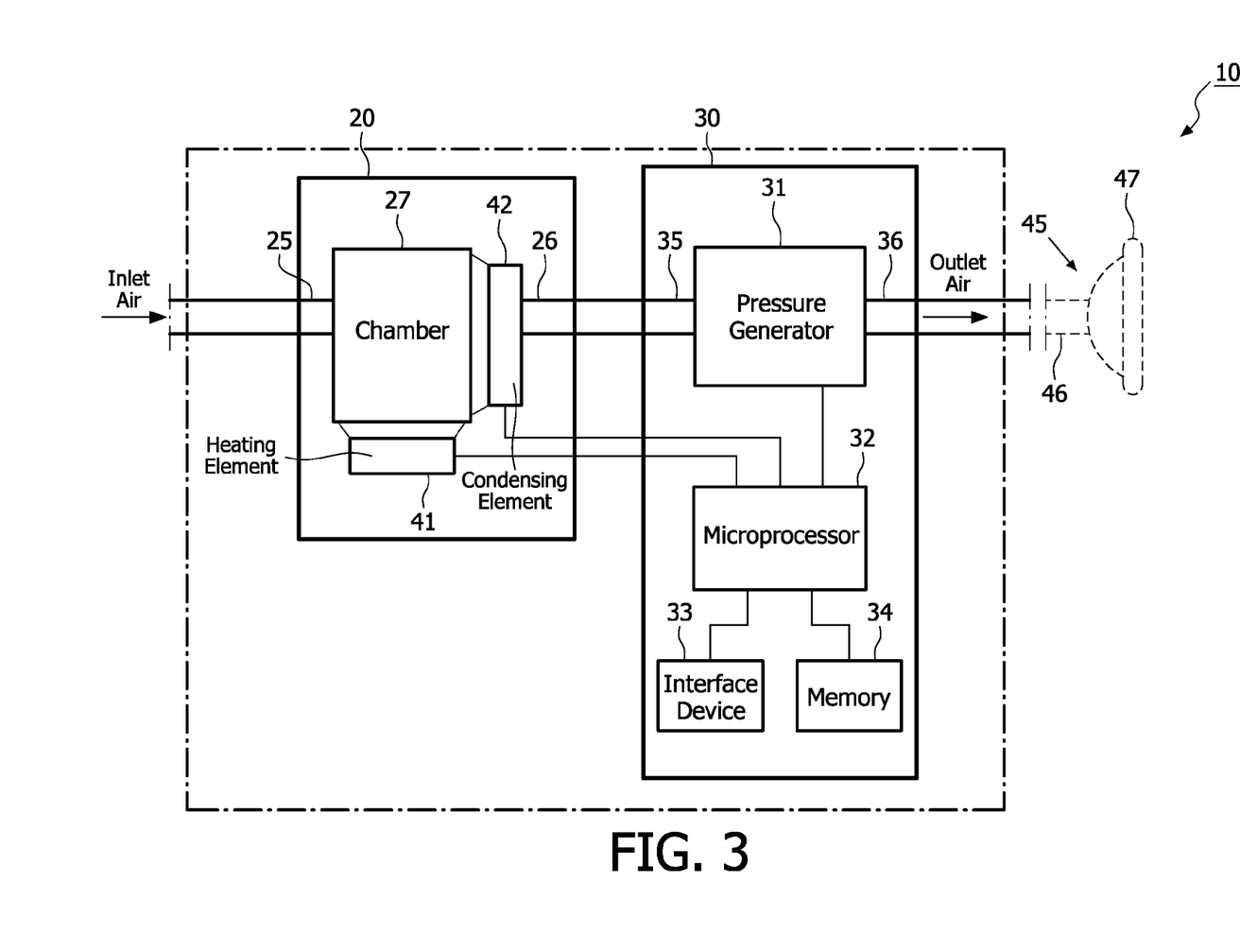
FIG. 3 is a schematic diagram of the pressure support system of FIG. 2.

Perspective and detailed schematic views of pressure support system 10 according to an exemplary embodiment of the present invention are generally illustrated in FIGS. 2 and 3, respectively. Pressure support system 10 is adapted to provide a regimen of respiratory therapy to a user and includes humidifier 20 and positive air pressure device 30, each of which are adapted to be detachably coupled with one other. As discussed above in conjunction with FIG. 1, pressure support system 10 is adapted to provide a humidified, pressurized flow of breathing gas to a user.

Positive air pressure device 30 is structured to generate a positive pressure flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Respironics, Inc. of Murrysville, Pa.), and auto-titration pressure support devices, among others.

A dry flow of breathing gas is drawn from the atmosphere into humidifier 20 through a gas inlet 25. The flow of breathing gas drawn from atmosphere is generally referred to herein as being "dry" because it typically has a lower relative humidity than desired and the relative humidity of this dry flow of breathing gas is typically increased inside humidifier 20. Gas inlet 25 is in fluid communication with a chamber 27 containing a supply of water with a free water surface. Water vapor present in chamber 27 from evaporation of the supply of water is entrained in the dry flow of breathing gas which passes over and/or impinges upon the free surface of the water. As a result, the relative humidity of the dry flow of breathing gas increases such that a humidified flow of breathing gas exits humidifier 20 at a gas outlet 26.

In the current embodiment, humidifier 20 includes a heating element 41 and a condensing element 42. Heating element 41 is structured to increase the temperature of the supply of water held within chamber 27. By heating the supply of water, the rate of evaporation, and thus the amount of water vapor available for entrainment, is increased. In contrast, condensing element 42 is structured to decrease the relative humidity of the humidified flow of breathing gas discharged from chamber 27. Condensing element 42 has a cooling surface which lowers the temperature of the portion of the humidified flow of breathing gas passing over the cooling surface and causes some of the water vapor in the humidified flow of breathing gas to rainout in a controlled manner. In the current embodiment, condensing element 42 is constructed using a Peltier device; although other devices or means may be used without departing from the scope of the present invention.

Although the discussion herein generally relates to using humidifier 20 to increase the amount of water vapor that is entrained in a dry flow of breathing gas, it is contemplated that pressure support system 10 may be employed to decrease the amount of water vapor entrained in a humidified flow of breathing gas while remaining within the scope of the present invention. For example, condensing element 42 may be employed such that the relative humidity of the flow of breathing gas exiting humidifier 20 is less than the relative humidity of the flow of breathing gas entering humidifier 20.

Gas outlet 26 is in fluid communication with a gas intake 35 of positive air pressure device 30. Gas intake 35 is adapted to receive the humidified flow of breathing gas from gas outlet 26 and deliver the same to a pressure generator 31. Pressure generator 31 is structured to generate a positive pressure flow of breathing gas from the humidified flow of breathing gas supplied from humidifier 20. In an exemplary embodiment, pressure generator 31 is a centrifugal blower in which a fan or impeller is driven by a motor operating under the control of a microprocessor 32. It is to be understood, however, that the present invention contemplates other techniques for generating a flow of breathing gas at an elevated pressure. For example, a drag compressor, fan, piston, or bellows, can also be used as pressure generator 31 in the positive pressure support system 10 to create the flow of breathing gas at a pressure greater than the ambient atmospheric pressure. The positive pressure flow of breathing gas generated by pressure generator 31 is discharged through a gas discharge 36 and is typically delivered to a user through, for example, a patient circuit 45 that includes a patient conduit 46 and a patient interface device 47. Patient circuit 45 is structured to communicate the flow of breathing gas from positive air pressure device 30 to the airway of a user. Typically, patient circuit 45 includes a conduit or tube 46, a first end of which couples with positive air pressure device 30 and a second end of which couples with patient interface device 47. Patient interface device 47 is typically a nasal or nasal/oral mask structured to be placed on and/or over the face of a patient. Any type of patient interface device 47, however, which facilitates the delivery of the flow of breathing gas to, and the removal of a flow of exhalation gas from, the airway of such a patient may be used while remaining within the scope of the present invention.

Positive air pressure device 30 includes a microprocessor 32, a user interface device 33, and a memory 34. Microprocessor 32 is adapted to implement and/or execute a number of operating routines. The operating routines may be in any of a variety of forms such as, without limitation, software, firmware, and the like which are executable by microprocessor 32. In the current embodiment, the operating routines are generally stored within memory 34 which is in operable communication with microprocessor 32. The operating routines may include instructions that, for example and without limitation, when executed by microprocessor 32 control the operation of pressure generator 31, heating element 41, and condensing element 42 to provide a regimen of respiratory therapy to a user.

Memory 34 provides storage for, among others, the number of routines executable by microprocessor 32. Memory 34 can be any of a variety of types of internal and/or external storage media such as, without limitation, RAM, ROM, EPROM(s), EEPROMS(s), and the like that provide a register for data storage such as in the fashion of an internal storage area of a computer, and can be volatile memory or nonvolatile memory.

User interface device 33 is structured to exchange information between positive air pressure device 30 and, for instance, a user. Examples of user interface devices 33 include manually actuated buttons, displays, keypads, voice activated input devices, audio outputs, indicators (e.g., lights), switches, knobs, modems, and networking cards, among others. As seen in FIG. 2, positive air pressure device 30 has a number of manually actuated buttons 33 that may be used, for example, to select the desired relative humidity level of the positive pressure flow of gas delivered to a user.

Table 2 (below) is an exemplary illustration of the rainout protection provided by placing humidifier 20 upstream of positive air pressure device 30 according to principles of the present invention. As stated above, when the temperature of the flow of breathing gas increases, so too does the amount of water vapor that the flow of breathing gas is capable of entraining therein. Because the flow of breathing gas is capable of holding more water vapor, the relative humidity (which is the ratio of the amount of water vapor being held to the amount of water vapor capable of being held) of the flow of breathing gas decreases.

As seen in Table 2, the temperature of the flow of breathing gas increases from 25° C. (77° F.) at gas outlet 26 to 26° C. (78.8° F.) at gas intake 35; correspondingly the relative humidity of the flow of breathing gas decreases from 100% to 94%. Because the relative humidity of the flow of breathing gas is less than 100% at gas intake 35, rainout does not occur. Although the relative humidity of the flow of breathing gas at gas outlet 26 is shown as 100% in Table 2, it is contemplated that a lower relative humidity may be achieved, for instance, using condensing element 42, to provide a greater safety margin.

Referring again to Table 2, the temperature of the flow of breathing gas increases from 26° C. (78.8° F.) at gas intake 35 to 32° C. (89.6° F.) at gas discharge 36 generally due to heat produced within pressure generator 31 by the work of air compression. With this increase in temperature, the relative humidity of the flow of breathing gas correspondingly decreases from 94% at gas intake 35 to 68% at gas discharge 36, thereby further lowering the risk of rainout occurring within positive air pressure device 30.

With pressure support system 10, testing has shown that the temperature increase imparted on the flow of breathing gas by pressure generator 31 (for example, due to the work of air compression) is substantially the same as the temperature decrease experienced by the flow of breathing gas as it passes through a standard 6 ft. length of patient conduit 46. This is illustrated in Table 2, for example, where the temperature of the flow of breathing gas increases 6° C. (10.8° F.) (i.e., from 26° C. (78.8° F.) to 32° C. (89.6° F.)) between gas intake 35 and gas discharge 36 and then decreases that same amount (i.e., 6° C. (10.8° F.)) between gas discharge 36 and the patient end of patient conduit 46.

As the temperature of the flow of breathing gas decreases, the amount of water vapor that can be entrained therein also decreases, thereby causing the relative humidity of the breathing gas to increase. Because the temperature of the flow of breathing gas at gas intake 35 and the patient end of patient conduit 46 are the same, the relative humidity of the flow of breathing gas at both of these points is also the same, here 94%. Accordingly, by maintaining the relative humidity of the flow of breathing gas at gas intake 35 at less than 100%, rainout within positive air pressure device 30 and patient circuit 45 is eliminated.

Although condensing element 42 is illustrated as being located upstream of pressure generator 31 in FIG. 3, it is contemplated that condenser element 42 can be located at a different location, for example and without limitation between pressure generator 31 and patient circuit 45, to insure that rainout does not occur within patient circuit 45. Likewise, it is contemplated that more than one condensing element 42 may be employed. For example, a first condensing element 42 may be located upstream of the pressure generator 31 (for instance, as shown in FIG. 3) and a second condensing element 42 may be located between pressure generator 31 and patient circuit 45. Other arrangements within the scope of the present invention are also contemplated.

Table 2 also illustrates that placing humidifier 20 upstream of positive air pressure device 30 limits the amount of water vapor that can be entrained within the flow of breathing gas by humidifier 20. For example, the flow of breathing gas inside humidifier 20 is at a temperature of 25° C. (77° F.). At this temperature, the maximum amount of water vapor that can be entrained in the flow of breathing gas is 22.8 mg/L. Because there is less water vapor entrained within the flow of breathing gas (as compared to the 26 mg/L of water vapor entrained in the flow of breathing gas of the known pressure support system; see Table 1), the risk of rainout within positive air pressure device 30 and patient circuit 45 is reduced.

Figure 4:
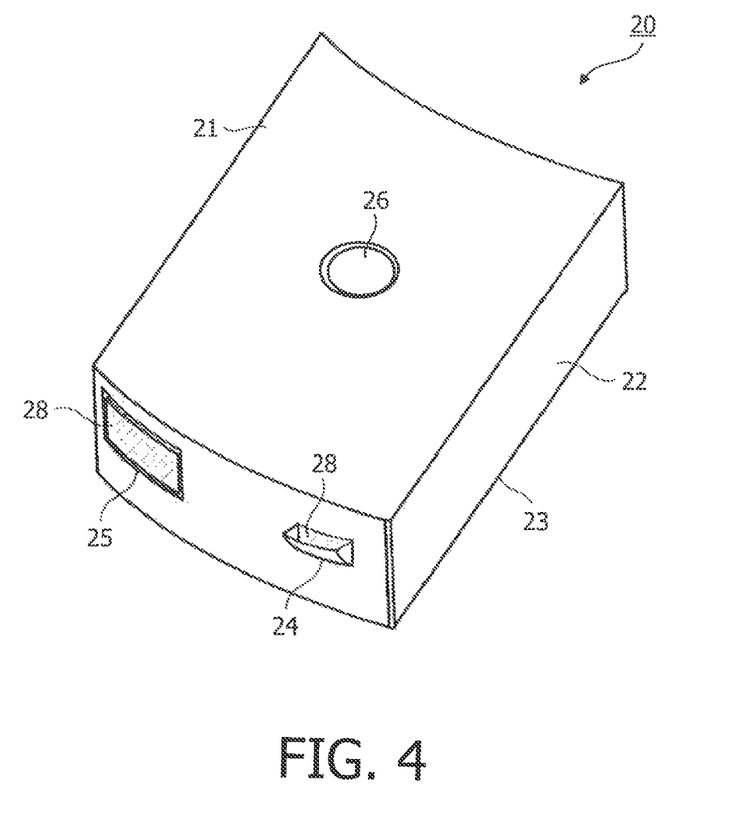
FIG. 4 is a perspective view, with a partial cut-away view, of the humidifier for the pressure support system shown in FIG. 2.

FIG. 4 is a perspective view of the humidifier 20 of FIG. 2 according to one embodiment of the present invention. Humidifier 20 includes a top wall 21, a substantially upright sidewall 22, and a bottom wall 23. Top wall 21, sidewall 22, and bottom wall 23 define a chamber 27 which is structured to hold a supply of water having a free water surface. A water fill port 24, which is in fluid communication with chamber 27, is

TABLE 2

Humidifier Upstream of the Positive Air Pressure Device

| | Water/Air Concentration (mg/L) | Temp. (Deg C.) | Sat. Vapor Pressure (Pa) | Vapor Pressure (Pa) | Humidity (RH %) |
|---|---|---|---|---|---|
| Ambient Air | 11.4 | 25.0 | 3148 | 1569 | 50 |
| Gas Outlet (Humidifier) | 22.8 | 25.0 | 3148 | 3139 | 100 |
| Gas Intake (PAP) | 22.8 | 26.0 | 3340 | 3149 | 94 |
| Pressure Generator | 22.8 | 26.0 | 3340 | 3149 | 94 |
| Gas Discharge (PAP) | 22.8 | 32.0 | 4718 | 3212 | 68 |
| Wall of Patient Conduit at Patient End | 22.8 | 26.0 | 3340 | 3149 | 94 | adapted to allow a user to easily re-fill chamber 27 with water. Chamber 27 may include a number of baffles and/or other structures adapted to promote entrainment of water vapor with the flow of breathing gas.

As stated above, a flow of breathing gas is drawn from the atmosphere through gas inlet 25 into humidifier 20. Gas inlet 25 is in fluid communication with chamber 27 and is structured to supply the flow of breathing gas to chamber 27. A gas outlet 26, which is also in fluid communication with chamber 27, is structured to discharge a humidified flow of breathing gas from chamber 27. Gas outlet 26 is adapted to fluidly couple with gas intake 35 of the positive air pressure device 30 shown in FIG. 2.

In the current embodiment, gas inlet 25 and water fill port 24 are disposed on the front of sidewall 22; whereas gas outlet 26 is disposed on top wall 21. It is contemplated, however, that alternative locations may be used while remaining within the scope of the present invention. Gas inlet 25 and water fill port 24 each have a filter element 28 associated therewith. Filter elements 28 are adapted to remove contaminants from the flow of breathing gas and/or the water supplied to chamber 27. Although shown as separate components in the current embodiment, it is contemplated that gas inlet 25 and water fill port 24 may be combined into a single component without departing from the scope of the present invention. It is further contemplated that filter element 28 may be adapted to remove contaminates from one or both of the flow of breathing gas and the supply of water.

Figure 5:
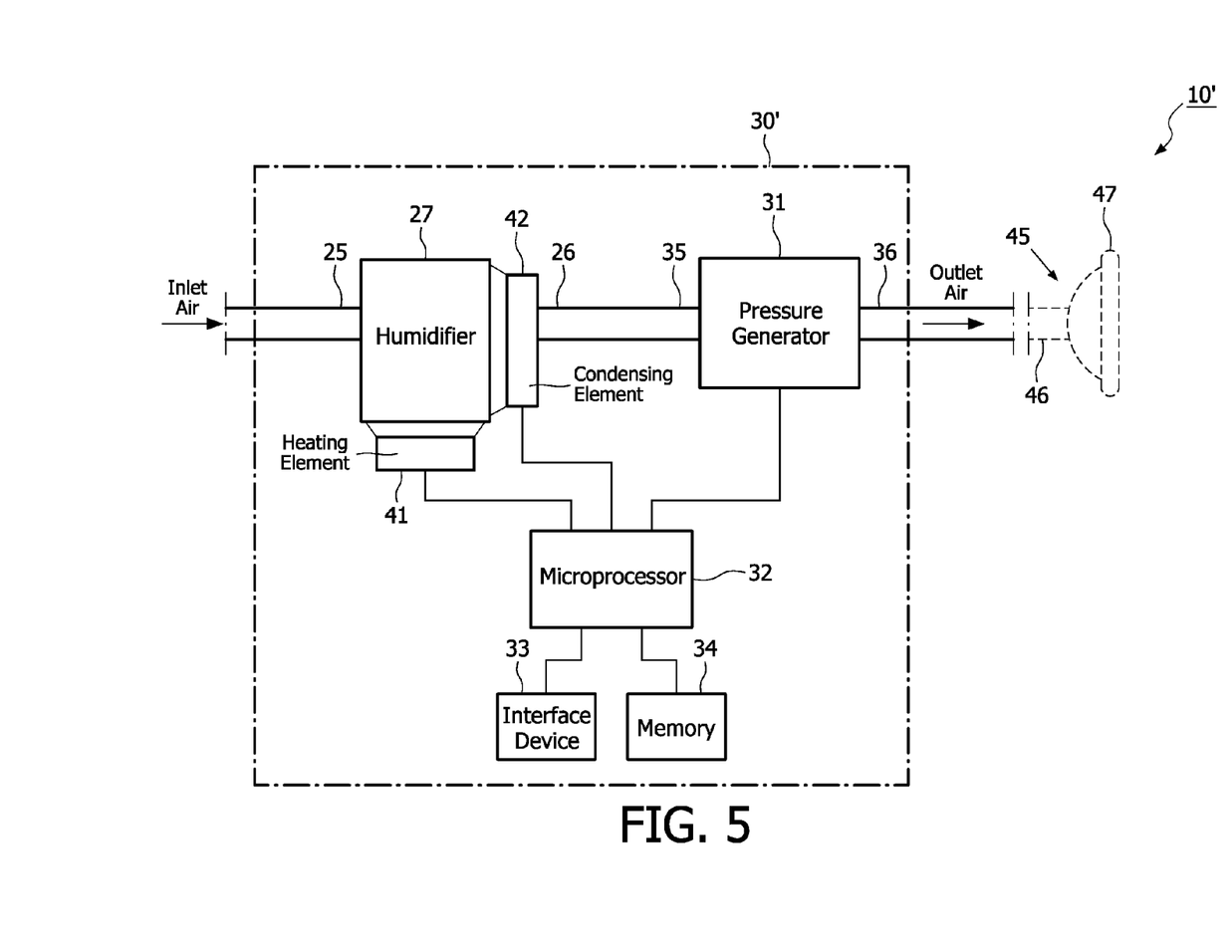
FIG. 5 is a schematic diagram of a pressure support system adapted to provide a regimen of respiratory therapy to a patient according to another embodiment.

Although pressure support system 10 is discussed in conjunction with a specific arrangement of components, it is contemplated that other arrangements, components, and/or combinations may be used to generate a positive pressure flow of breathing gas within the scope of the present invention. For example, although humidifier 20 is generally illustrated and described as an evaporative type humidifier, other types of humidifiers such as, vaporizing humidifiers, ultrasonic humidifiers, and atomizing humidifiers, among others, may be employed without departing from the scope of the present invention. As another example, although humidifier 20 and positive air pressure device 30 are illustrated as separate components in FIG. 3, a pressure support system 10' in which the components of humidifier 20 are incorporated into a positive air pressure device 30' (See FIG. 5) is also contemplated which does not depart from the scope of the present invention. As yet another example, it is contemplated that humidifier 20 and/or positive air pressure device 30 may have a water ingress valve structured to prevent water ingress into gas intake 35 from gas outlet 26.

Figure 6:
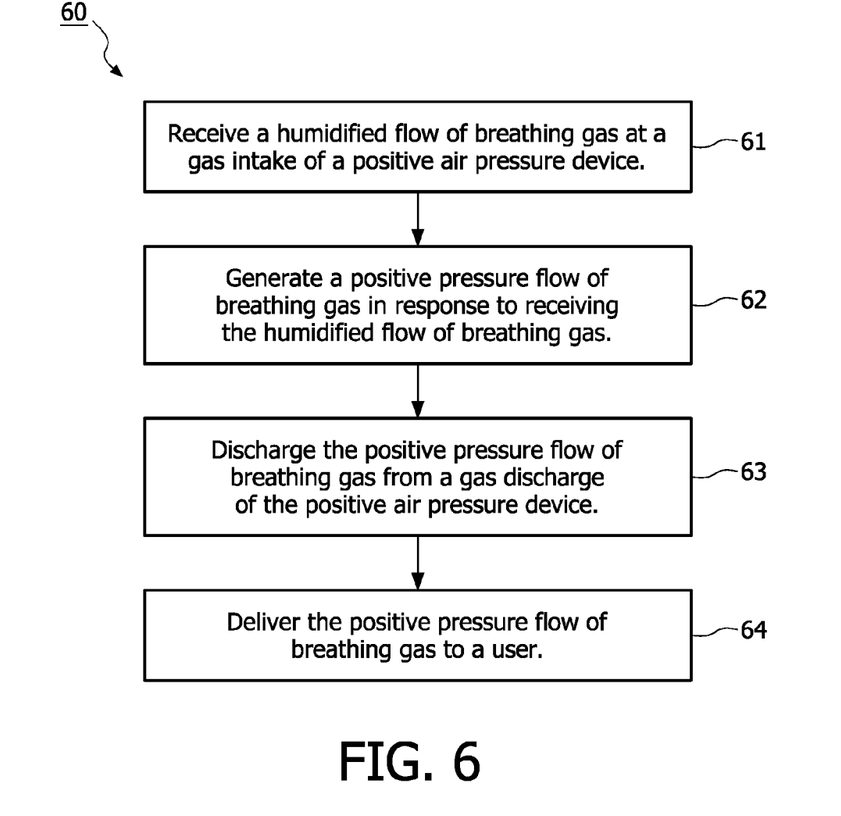
FIG. 6 illustrates an operational process for providing a regimen of respiratory therapy to a patient according to one embodiment.

An operational process 60 for providing a regimen of respiratory therapy to a user according to one embodiment is illustrated in FIG. 6. Operational process begins with operation 61 where a humidified flow of breathing gas is received at a gas intake of a positive air pressure device. In the current embodiment, for example, a dry flow of breathing gas is received at gas inlet 25 of humidifier 20. Humidifier 20 is employed to generate the humidified flow of breathing gas. For example, a flow of gas having a temperature of 25° C. (77° F.) and a relative humidity of 50% is pulled from the atmosphere and supplied to gas inlet 25. This dry flow of breathing gas is passed through chamber 27 in humidifier 20. Chamber 27 is structured to hold a supply of water. The dry flow of breathing gas passes over and/or impinges upon a free surface of the water. Water vapor present as a result of evaporation of the supply of water within chamber 27 is entrained in the dry flow of breathing gas. As a result, the relative humidity of the dry flow of breathing gas is increased from 50% to 100%. Thus, the flow of breathing gas is now a humidified flow of breathing gas. The humidified flow of breathing gas is then supplied to gas intake 35 of positive air pressure device 30 from gas outlet 26 of humidifier 20.

A heating element and/or a condensing element associated with the humidifier may be used to control the amount of water vapor entrained in the flow of breathing gas. In the current embodiment, heating element 41 is generally employed to increase the relative humidity of the flow of breathing gas passing through humidifier 20; whereas condensing element 42 is generally employed to decrease the relative humidity of the flow of breathing gas passing through humidifier 20. Heating element 41 is structured to increase the temperature of the supply of water held within chamber 27. This heating increases the rate of evaporation associated with the supply of water; thereby increasing the amount of water vapor available to be entrained within of the flow of breathing gas passing through chamber 27.

In contrast, condensing element 42 provides a cool surface, which when passed over and/or impinged upon by the flow of breathing gas, causes some amount of the water vapor entrained within the flow of breathing gas to condense. For instance, it may be desirable to reduce the relative humidity of the humidified flow of breathing gas from 100% to 95% in order to provide an additional safety margin against rainout within the pressure generating device 10. Condensing element 42 may be constructed using, for example and without limitation, a Peltier device; although other devices or means within the scope of the present invention are contemplated.

Operational control is then passed to operation 62 where, in response to receiving the humidified flow of breathing gas, a positive pressure flow of breathing gas is generated with the positive air pressure device. In the current embodiment, the humidified flow of breathing gas, having a temperature of 25° C. (77° F.) and a relative humidity of 100%, is received by positive air pressure device 30. The humidified flow of breathing gas is pressurized to become the positive pressure flow of breathing gas. As the humidified flow of breathing gas is pressurized, its temperature increases while its relative humidity correspondingly decreases. In the current example, for instance, the temperature of the humidified flow of breathing gas increases from 25° C. (77° F.) to 32° C. (89.6° F.); while the relative humidity of the humidified flow of breathing gas correspondingly decreases from 100% to 68%.

Operational control is then passed to operation 63 where the positive pressure flow of breathing gas is discharged from a gas discharge of the positive air pressure device. In the current embodiment, the positive pressure flow of breathing gas discharged from positive air pressure device 30 has a temperature of 32° C. (89.6° F.) and a relative humidity of 68%. The positive pressure flow of breathing gas is discharged from gas discharge 36 and communicated to patient circuit 45.

Operational control is then passed to operation 64 where the positive pressure flow of breathing gas is delivered to a user. In the current embodiment, the positive pressure flow of breathing gas is delivered to a user via patient circuit 45. Here, patient circuit 45 includes a standard 6 ft. patient conduit 46 and a patient interface device 47 (such as and without limitation, a nasal mask, a full-face mask, a total face mask, and nasal cannulas, among others). Because the walls of patient conduit 46 are generally at the ambient temperature of 25° C. (77° F.), heat loss occurs as the positive pressure flow of breathing gas passes through patient conduit 46. In the current embodiment, the positive pressure flow of air decreases in temperature from 32° C. (89.6° F.) to 26° C. (78.8° F.) before it is delivered to the patient. Correspondingly, the relative humidity of the positive pressure flow of breathing gas increases from 68% to 94%. The relative humidity of the positive pressure flow of breathing gas, after being discharged from gas outlet 26 of humidifier 20, never reaches 100%. Thus, rainout is prevented in the positive air pressure device 30 and in patient circuit 45. In one embodiment, a condensing element 42 is located between pressure generator 31 and patient circuit 45, to further insure that rainout does not occur within patient circuit 45.

It should be noted that the temperature and relative humidity values illustrated in Table 2 and discussed in conjunction with operational process 60 are exemplary. It is contemplated that other temperature and relative humidity values may be employed while remaining within the scope of the present invention. Generally, the present invention contemplates a method for providing a regimen of respiratory therapy to a user in which a flow of breathing gas received at gas intake 35 has a first temperature and a first relative humidity. Positive air pressure device 30 uses this flow of breathing gas to generate a positive pressure flow of breathing gas that has a second temperature and a second relative humidity. This positive pressure flow of breathing gas is delivered to a patient. Due to temperature losses experienced during delivery, however, the positive pressure flow of breathing gas delivered to the patient has third temperature and a third relative humidity. The present invention manages the temperature and relative humidity of the flow of breathing gas so that the first temperature is less than the second temperature but substantially the same as the third temperature and the first relative humidity is greater than the second relative humidity but substantially the same as the third relative humidity. Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A pressure support system, comprising:
a humidifier adapted to increase the amount of water vapor entrained in a supply of breathing gas and output a first flow of humidified breathing gas, the first flow of humidified breathing gas having a first temperature and a first relative humidity;
a positive air pressure device fluidly coupled downstream of the humidifier, wherein the positive air pressure device has a gas intake for receiving the first flow of humidified breathing gas, wherein the positive air pressure device is structured to generate a positive pressure flow of humidified breathing gas from the first flow of humidified breathing gas, the positive pressure flow of humidified breathing gas having a second temperature and a second relative humidity at a gas discharge of the positive air pressure device; and
a patient circuit having a first end coupled to the gas discharge of the positive air pressure device for receiving the positive pressure flow of humidified breathing gas and a patient end opposite the first end, wherein the positive air pressure device and the patient circuit are structured to cause the positive pressure flow of humidified breathing gas at the patient end of the patient circuit to have a third temperature and a third relative humidity, wherein the first temperature is less than the second temperature and the first relative humidity is greater than the second relative humidity, and wherein the first temperature is substantially the same as the third temperature and the first relative humidity is substantially the same as the third relative humidity.

2. The pressure support system of claim 1, wherein the humidifier comprises:
a chamber structured to hold a supply of water having a free water surface;
a gas inlet structured to admit the supply of breathing gas into the chamber, and
a gas outlet structured to discharge the first flow of humidified breathing gas from the chamber.

3. The pressure support system of claim 2, the gas intake of the positive air pressure device is fluidly coupled with the gas outlet of the humidifier.

4. The pressure support system of claim 2, further comprising at least one of:
a heating element structured to increase the temperature of the supply of water held within the chamber; and
a condensing element structured to decrease the amount of water vapor entrained in the supply of breathing gas and at least partially cause the first flow of humidified breathing gas at the gas intake to have a relative humidity that is less than 100%.

5. The pressure support system of claim of claim 4, wherein the positive air pressure device further comprises:
a number of sensors adapted to sense at least one of temperature and humidity; and
a processor adapted to communicate with the number of sensors and, in response thereto, to control at least one of the heating element and the condensing element to maintain the amount of water vapor entrained within the first flow of humidified breathing gas discharged from the chamber at a level which prevents rainout within the positive air pressure device.

6. A method for providing a flow of humidified breathing gas, comprising:
receiving a first flow of humidified breathing gas at a gas intake of a positive air pressure device, the first flow of humidified breathing gas having a first temperature and a first relative humidity;
generating a positive pressure flow of humidified breathing gas with the positive air pressure device, the positive pressure flow of humidified breathing gas having a second temperature and a second relative humidity at a gas discharge of the positive air pressure device; and
delivering the positive pressure flow of humidified breathing gas to a patient circuit having a first end coupled to the gas discharge of the positive air pressure device and a patient end opposite the first end, wherein the positive pressure flow of humidified breathing gas at the patient end of the patient circuit has a third temperature and a third relative humidity, wherein the first temperature is less than the second temperature and the first relative humidity is greater than the second relative humidity, and wherein the first temperature is substantially the same as the third temperature and the first relative humidity is substantially the same as the third relative humidity.

7. The method of claim 6, wherein the first relative humidity and the third relative humidity are less than 100%.

* * * * *